US012676224B2

(12) United States Patent (10) Patent No.: US 12,676,224 B2
Cescon et al. (45) Date of Patent: Jul. 7, 2026

(54) SYSTEM AND METHOD FOR PREDICTING BLOOD-GLUCOSE CONCENTRATION

(71) Applicant: University of Houston System, Houston, TX (US)

(72) Inventors: Marzia Cescon, Houston, TX (US); Mehrad Jaloli, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 951 days.

(21) Appl. No.: 17/889,611

(22) Filed: Aug. 17, 2022

(65) Prior Publication Data

US 2023/0058548 A1 Feb. 23, 2023

Related U.S. Application Data

(60) Provisional application No. 63/234,422, filed on Aug. 18, 2021.

(51) Int. Cl.
| | |
|---|---|
| *G16H 20/17* | (2018.01) |
| *A61M 5/172* | (2006.01) |
| *G16H 50/20* | (2018.01) |

(52) U.S. Cl.
CPC .......... *G16H 20/17* (2018.01); *A61M 5/1723* (2013.01); *G16H 50/20* (2018.01); *A61M 2230/201* (2013.01)

(58) Field of Classification Search
None
See application file for complete search history.

(56) References Cited

U.S. PATENT DOCUMENTS

2020/0170578 A1\* 6/2020 Park .................... A61B 5/7264
2021/0068669 A1\* 3/2021 Bidet .................... G16H 50/20

FOREIGN PATENT DOCUMENTS

WO 2021007391 A1 1/2021

OTHER PUBLICATIONS

Jaloli, Mehrad, et al.,. "Long-term Prediction of Blood Glucose Levels in Type 1 Diabetes Using a CNN-LSTM-Based Deep Neural Network," Journal of Diabetes Science and Technology, Apr. 2022, 19322968221092785.

(Continued)

*Primary Examiner* — Manuel A Mendez
(74) *Attorney, Agent, or Firm* — Carter, DeLuca & Farrell LLP; George Likourezos

(57) ABSTRACT
A system for predicting blood-glucose concentration includes a blood-glucose monitoring device including a sensor configured to capture blood-glucose levels, a processor, and a memory. The memory includes instructions, which, when executed by the processor, cause the system to: access data of meal intake for a person with type 1 diabetes, data of insulin doses administered to the person, data corresponding to a physical activity of the person, and data of blood-glucose levels in the person, captured by the sensor; predict by a deep learning network blood-glucose concentration levels for the person at predetermined time intervals based on the accessed data of meal intake, data of insulin doses, data corresponding to the physical activity, and data of blood-glucose levels in the person; and determine an insulin administration schedule based on the predicted blood-glucose concentration levels for the person, the insulin administration schedule including a dosing schedule.

20 Claims, 9 Drawing Sheets

(56) References Cited

OTHER PUBLICATIONS

Jaloli, Mahrad, et al., "Predicting Blood Glucose Levels Using CNN-LSTM Neural Networks," Department of Mechanical Engineering, University of Houston, Poster Oct. 2020 Diabetes Technology Meeting, 1 page.

Li, Kezhi, et al. "GluNet: A deep learning framework for accurate glucose forecasting," IEEE journal of biomedical and health informatics, Jul. 2019, pp. 414-423, 24.2.

Zhu, Taiyu, et al., "A Deep Learning Algorithm for Personalized Blood Glucose Prediction," KHD@ IJCAI, Jul. 2018, pp. 64-78.

Mirshekarian, Sadegh, et al., "LSTMs and neural attention models for blood glucose prediction: Comparative experiments on real and synthetic data," 2019 41st annual international conference of the IEEE engineering in medicine and biology society (EMBC). IEEE, Jul. 2019, pp. 706-712.

Mirshekarian, Sadegh, et al., "Using LSTMs to learn physiological models of blood glucose behavior," 2017 39th Annual International Conference of the IEEE Engineering in Medicine and Biology Society (EMBC), IEEE, Jul. 2017, pp. 2887-2891.

Li, Kezhi, et al., "Convolutional recurrent neural networks for glucose prediction," IEEE journal of biomedical and health informatics, Apr. 2019, pp. 603-613, 24.2.

International Preliminary Report on Patentability issued by the International Bureau of WIPO in connection with International Application No. PCT/US2022/040550, dated Feb. 13, 2024.

International Search Report and Written Opinion for corresponding case PCT/US22/40550, Dec. 13, 2022, 8 pages.

* cited by examiner

400

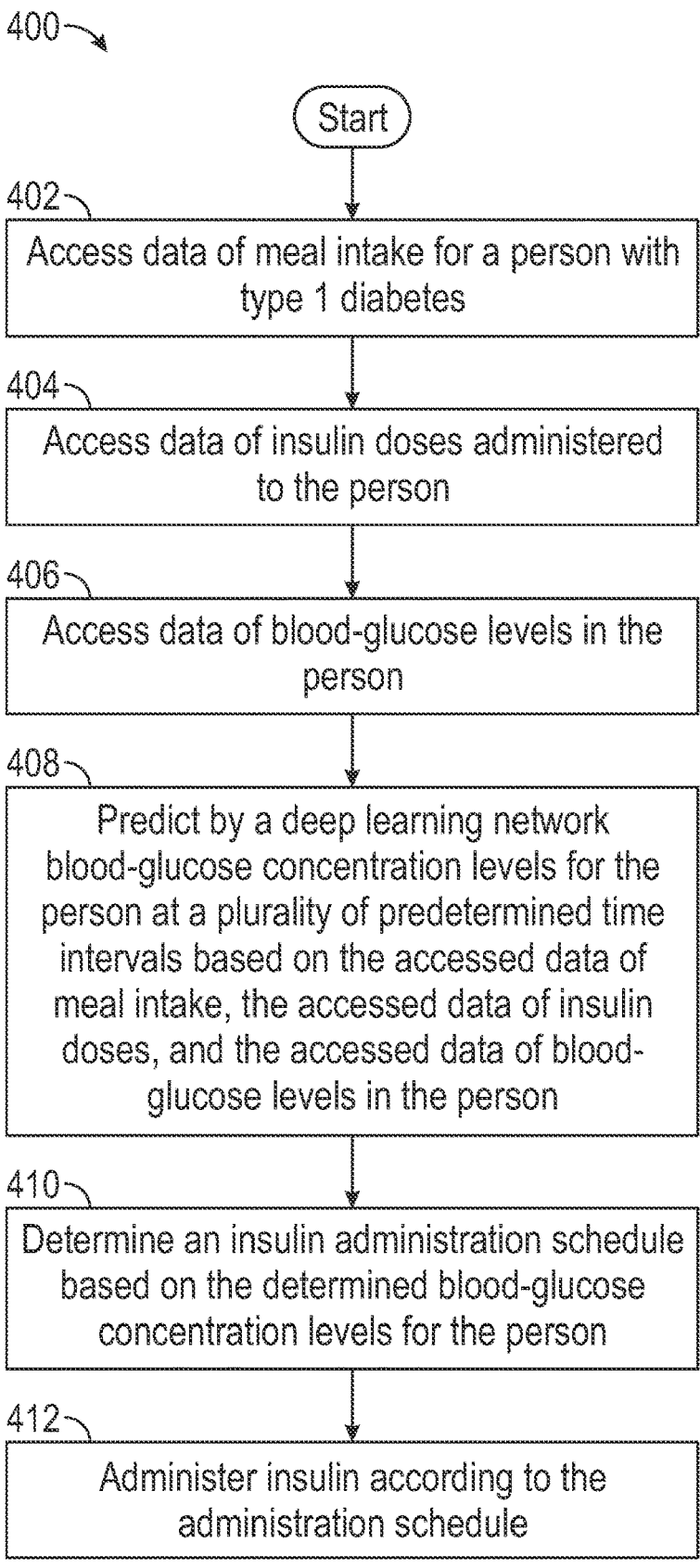

Start

402

Access data of meal intake for a person with type 1 diabetes

404

Access data of insulin doses administered to the person

406

Access data of blood-glucose levels in the person

408

Predict by a deep learning network blood-glucose concentration levels for the person at a plurality of predetermined time intervals based on the accessed data of meal intake, the accessed data of insulin doses, and the accessed data of blood-glucose levels in the person

410

Determine an insulin administration schedule based on the determined blood-glucose concentration levels for the person

412

Administer insulin according to the administration schedule

FIG. 4

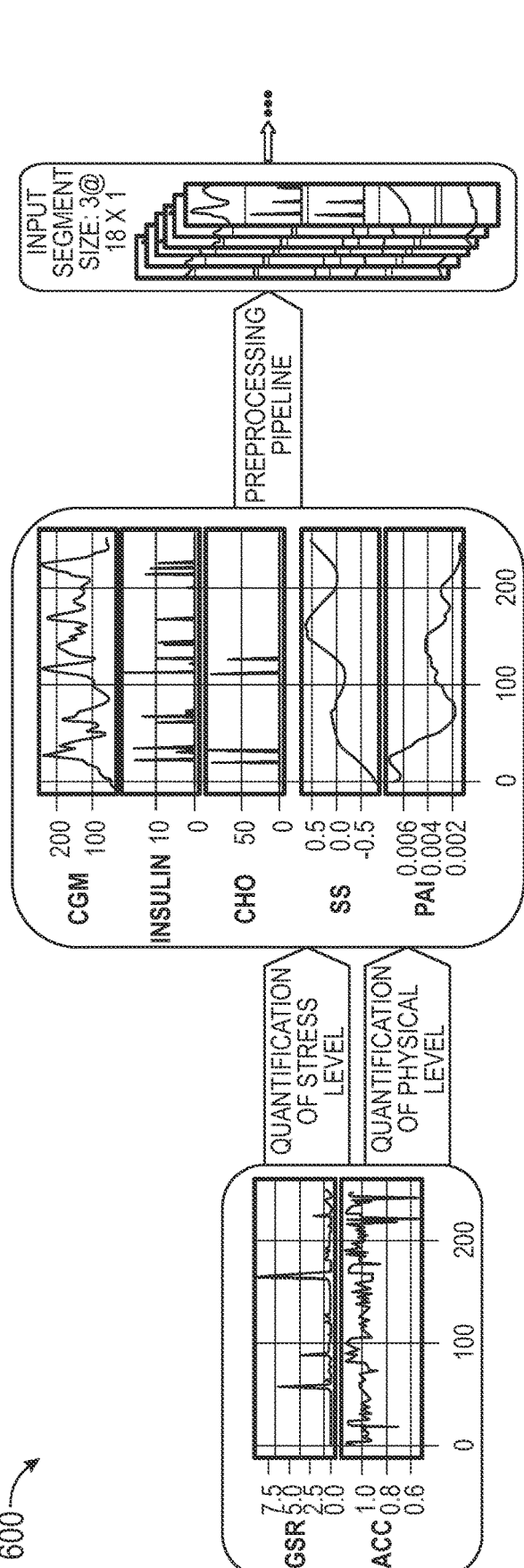
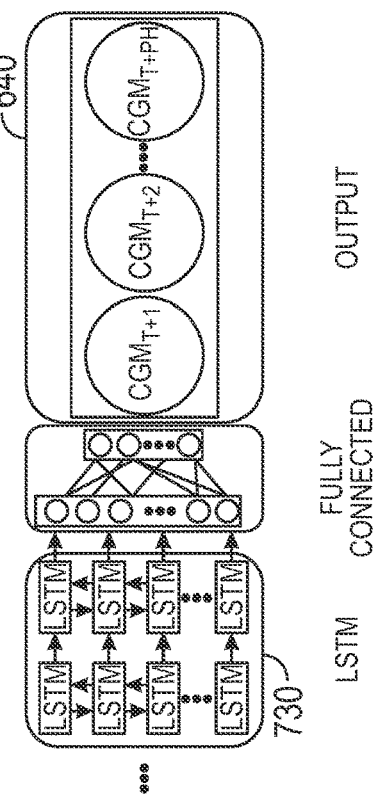
FIG. 6

| Scenario | 30 Min | | | 60 Min | | | 90 Min | | |
|---|---|---|---|---|---|---|---|---|---|
| | RMSE [mg/dL] | MAE [mg/dL] | R2 [%] | RMSE [mg/dL] | MAE [mg/dL] | R2 [%] | RMSE [mg/dL] | MAE [mg/dL] | R2 [%] |
| 1 | 18.32 | 12.98 | 91.54 | 33.26 | 22.98 | 66.92 | 48.76 | 37.11 | 49.76 |
| 2 | 17.64 | 12.54 | 92.11 | 32.12 | 21.44 | 69.61 | 47.21 | 35.11 | 52.09 |
| 3 | 17.98 | 12.81 | 91.12 | 31.07 | 20.98 | 69.30 | 46.98 | 34.60 | 53.22 |
| 4 | 12.47 | 9.93 | 94.35 | 26.27 | 18.05 | 77.12 | 42.90 | 32.65 | 55.74 |
| 5 | 16.88 | 11.97 | 93.12 | 32.15 | 19.91 | 70.34 | 45.65 | 33.65 | 54.33 |
| 6 | 17.11 | 12.10 | 92.43 | 31.11 | 19.59 | 71.54 | 45.11 | 32.88 | 55. |
| 7 | 12.35 | 9.13 | 95.34 | 24.71 | 17.75 | 78.87 | 41.64 | 31.85 | 60.11 |

FIG. 7

| Scenario | 30 Min | | | 60 Min | | | 90 Min | | |
|---|---|---|---|---|---|---|---|---|---|
| | RMSE [mg/dL] | MAE [mg/dL] | R2 [%] | RMSE [mg/dL] | MAE [mg/dL] | R2 [%] | RMSE [mg/dL] | MAE [mg/dL] | R2 [%] |
| 1 | 19.35 | 13.31 | 90.87 | 32.68 | 22.32 | 68.82 | 46.12 | 34.20 | 54.12 |
| 2 | 18.65 | 13.23 | 90.98 | 31.48 | 21.12 | 70.02 | 45.56 | 33.45 | 56.34 |
| 3 | 18.43 | 13.02 | 91.21 | 31.12 | 20.23 | 70.34 | 45.23 | 33.30 | 56.72 |
| 4 | 12.63 | 10.05 | 93.75 | 26.48 | 18.79 | 76.50 | 40.59 | 30.82 | 59.82 |
| 5 | 17.36 | 12.37 | 91.82 | 30.15 | 19.80 | 72.34 | 44.67 | 31.90 | 58.34 |
| 6 | 17.28 | 12.30 | 91.90 | 31.02 | 19.59 | 72.14 | 43.67 | 30.75 | 59.12 |
| 7 | 12.51 | 9.37 | 94.65 | 25.37 | 17.87 | 78.37 | 39.52 | 29.47 | 61.12 |

FIG. 8

| Patient ID | 30 Min | | | 60 Min | | | 90 Min | | |
|---|---|---|---|---|---|---|---|---|---|
| | RMSE [mg/dL] | MAE [mg/dL] | R2 [%] | RMSE [mg/dL] | MAE [mg/dL] | R2 [%] | RMSE [mg/dL] | MAE [mg/dL] | R2 [%] |
| 540 | 15.74 | 11.46 | 88.86 | 33.54 | 23.35 | 72.34 | 41.73 | 31.61 | 56.12 |
| 544 | 11.47 | 8.14 | 93.41 | 21.28 | 15.37 | 79.99 | 38.77 | 29.15 | 68.30 |
| 552 | 11.12 | 8.71 | 92.56 | 21.79 | 15.31 | 79.92 | 39.15 | 27.62 | 69.45 |
| 567 | 12.47 | 9.61 | 91.36 | 27.8 | 18.76 | 73.78 | 47.85 | 33.44 | 40.30 |
| 584 | 13.32 | 10.01 | 91.78 | 27.28 | 19.68 | 73.06 | 44.94 | 32.95 | 51.45 |
| 596 | 12.99 | 9.98 | 93.32 | 22.61 | 16.03 | 78.12 | 42.71 | 32.90 | 53.87 |
| Mean ± (STD) | 12.85± 1.50 | 9.65± 1.05 | 91.88± 1.54 | 25.71± 4.37 | 18.08± 2.89 | 76.20± 3.22 | 42.52± 3.17 | 31.27± 2.16 | 56.58± 10.01 |

FIG. 9

| Patient ID | 30 Min | | | 60 Min | | | 90 Min | | |
| --- | --- | --- | --- | --- | --- | --- | --- | --- | --- |
| | RMSE [mg/dL] | MAE [mg/dL] | R2 [%] | RMSE [mg/dL] | MAE [mg/dL] | R2 [%] | RMSE [mg/dL] | MAE [mg/dL] | R2 [%] |
| 540 | 16.12 | 13.45 | 86.76 | 33.45 | 23.11 | 69.56 | 40.12 | 30.61 | 58.11 |
| 544 | 12.98 | 9.98 | 91.65 | 23.65 | 16.11 | 77.67 | 38.56 | 29.11 | 69.35 |
| 552 | 12.12 | 9.56 | 90.56 | 23.11 | 16.23 | 77.34 | 39.05 | 27.88 | 69.65 |
| 567 | 13.98 | 11.34 | 90.36 | 26.44 | 18.87 | 71.12 | 46.11 | 32.41 | 47.89 |
| 584 | 14.56 | 12.18 | 90.78 | 26.87 | 19.54 | 71.76 | 44.35 | 31.66 | 52.41 |
| 596 | 14.06 | 12.01 | 91.32 | 24.11 | 17.05 | 76.54 | 41.12 | 32.40 | 56.57 |
| Mean ± (STD) | 13.97± 1.25 | 11.42± 1.32 | 90.23± 1.61 | 26.27± 3.50 | 18.48± 2.43 | 73.99± 3.26 | 41.55± 2.77 | 30.67± 1.69 | 58.99± 8.10 |

FIG. 10

SYSTEM AND METHOD FOR PREDICTING BLOOD-GLUCOSE CONCENTRATION

CROSS REFERENCE TO RELATED APPLICATION

This application claims the benefit of and priority to U.S. Provisional Patent Application Ser. No. 63/234,422, filed on Aug. 18, 2021, the entire contents of which are incorporated by reference herein.

TECHNICAL FIELD

The present disclosure relates to predicting blood-glucose concentration and, more specifically, to systems and methods for predicting blood-glucose concentration in a person with type 1 diabetes.

BACKGROUND

For people with type 1 diabetes (T1D), accurate forecasting of the blood glucose level is crucial for the appropriate regulation of glucose interventions. However, current techniques for predicting blood-glucose concentrations on an individual basis have demonstrated limited accuracy.

Accordingly, there is interest in data augmentation.

SUMMARY

An aspect of the present disclosure provides a system for predicting blood-glucose concentration includes a blood-glucose monitoring device includes a sensor configured to capture blood-glucose levels, a processor, and a memory. The memory includes instructions, which, when executed by the processor, cause the system to: access data of meal intake for a person with type 1 diabetes; access data of insulin doses administered to the person; access data corresponding to physical activity of the person; access data of blood-glucose levels in the person, captured by the sensor; predict by a deep learning network blood-glucose concentration levels for the person at a plurality of predetermined time intervals based on the accessed data of meal intake, the accessed data of insulin doses, the accessed data corresponding to physical activity of the person; the accessed data of blood-glucose levels in the person; and determine an insulin administration schedule based on the predicted blood-glucose concentration levels for the person, the insulin administration schedule including a dosing schedule.

In an aspect of the present disclosure, the system for predicting blood glucose concentration may include an insulin pump. The instructions stored on the memory may further cause the insulin pump to administer insulin according to the insulin administration schedule to the person.

In another aspect of the present disclosure, the instructions, when executed by the processor, may further cause the system to communicate the insulin administration schedule to the person.

In an aspect of the present disclosure, the instructions, when executed by the processor, may further cause the system to detect real-time blood glucose concentrations in the person during the insulin administration schedule and may modify the insulin administration schedule based on the detected real-time blood glucose concentrations in the person.

In another aspect of the present disclosure, the data of meal intake accessed by the processor may further include data of lipid, carbohydrate, and protein intake.

In an aspect of the present disclosure, the instructions, when executed by the processor, may cause the system to predict blood-glucose concentration levels for the person at about 30-minute, about 60-minute, and about 90-minute time intervals.

In another aspect of the present disclosure, the instructions, when executed by the processor, may further cause the system to receive historical glucose metabolism data for the person and may include the historical glucose metabolism data as a further input to the deep learning network.

In an aspect of the present disclosure, the instructions, when executed by the processor, may further cause the system to receive data of bolus doses and may correct doses received by the person during a predetermined time period.

In another aspect of the present disclosure, the system may further include at least one of a smartphone, tablet computer, or cloud-based application in communication with the blood-glucose monitoring device.

In an aspect of the present disclosure, the deep learning network may include a convolutional neural network and a long short-term memory network.

An aspect of the present disclosure provides a computer-implemented method for predicting blood-glucose concentration. The method includes accessing data of meal intake for a person with type 1 diabetes, accessing data of insulin doses administered to the person, and accessing data of blood-glucose levels in the person. The method also includes determining, by a deep learning network, the blood-glucose concentration levels for the person at a plurality of predetermined time intervals based on the accessed data of meal intake, the accessed data of insulin doses, and the accessed data of blood-glucose levels in the person, and determining an insulin administration schedule based on the predicted blood-glucose concentration levels for the person, the insulin administration schedule including a dosing schedule.

In an aspect of the present disclosure, the computer-implemented method may further include administering insulin to the person according to the determined insulin administration schedule.

In another aspect of the present disclosure, the insulin administered to the person may be administered by an insulin pump.

In an aspect of the present disclosure, the computer-implemented method may further include communicating the insulin administration schedule to the person.

In another aspect of the present disclosure, the computer-implemented method may further include detecting real-time blood glucose concentrations in the person during the insulin administration schedule and may include modifying the insulin administration schedule based on the detected real-time blood glucose concentrations in the person.

In an aspect of the present disclosure, the data of meal intake may further include data of lipid, carbohydrate, and protein intake.

In another aspect of the present disclosure, the plurality of predetermined time intervals may further include about 30-minute, about 60-minute, and about 90-minute time intervals.

In an aspect of the present disclosure, the computer-implemented method may further include providing historical glucose metabolism data for the person and may include the historical glucose metabolism data as a further input to the deep learning network.

In another aspect of the present disclosure, the data of insulin doses administered to the person may further include data of bolus doses and may include correction doses received by the person during a predetermined time period.

An aspect of the present disclosure provides a non-transitory computer-readable medium storing instructions which, when executed by a processor, causes the processor to perform a computer-implemented method for predicting blood-glucose concentration. The computer-implemented method includes accessing data of meal intake for a person with type 1 diabetes, accessing data of insulin doses administered to the person, and accessing data of blood-glucose levels in the person. The method further includes determining, by a deep learning network, blood-glucose concentration levels for the person at a plurality of predetermined time intervals based on the accessed data of meal intake, the accessed data of insulin doses, and the accessed data of blood-glucose levels in the person and determining an insulin administration schedule based on the predicted blood-glucose concentration levels for the person, the insulin administration schedule including a dosing schedule.

Further details and aspects of the present disclosure are described in more detail below with reference to the appended drawings.

BRIEF DESCRIPTION OF THE DRAWINGS

A better understanding of the features and advantages of the present disclosure will be obtained by reference to the following detailed description that sets forth illustrative aspects, in which the principles of the present disclosure are utilized, and the accompanying drawings of which:

FIG. 4 is a flow diagram of a computer-implemented method for predicting blood-glucose concentration, in accordance with aspects of the present disclosure;

FIG. 6 is a diagram of a LSTM network employed for making predictions, in accordance with aspects of the disclosure;

FIG. 7 is a table of population results for the LSTM network, in accordance with aspects of the disclosure;

FIG. 8 is a table of population results for the CNN-LSTM network, in accordance with aspects of the disclosure;

FIG. 9 is a table of patient-wise analysis results for the LSTM network, in accordance with aspects of the disclosure; and FIG. 10 is a table of patient-wise analysis results for the CNN-LSTM network, in accordance with aspects of the disclosure.

DETAILED DESCRIPTION

Figure 1:
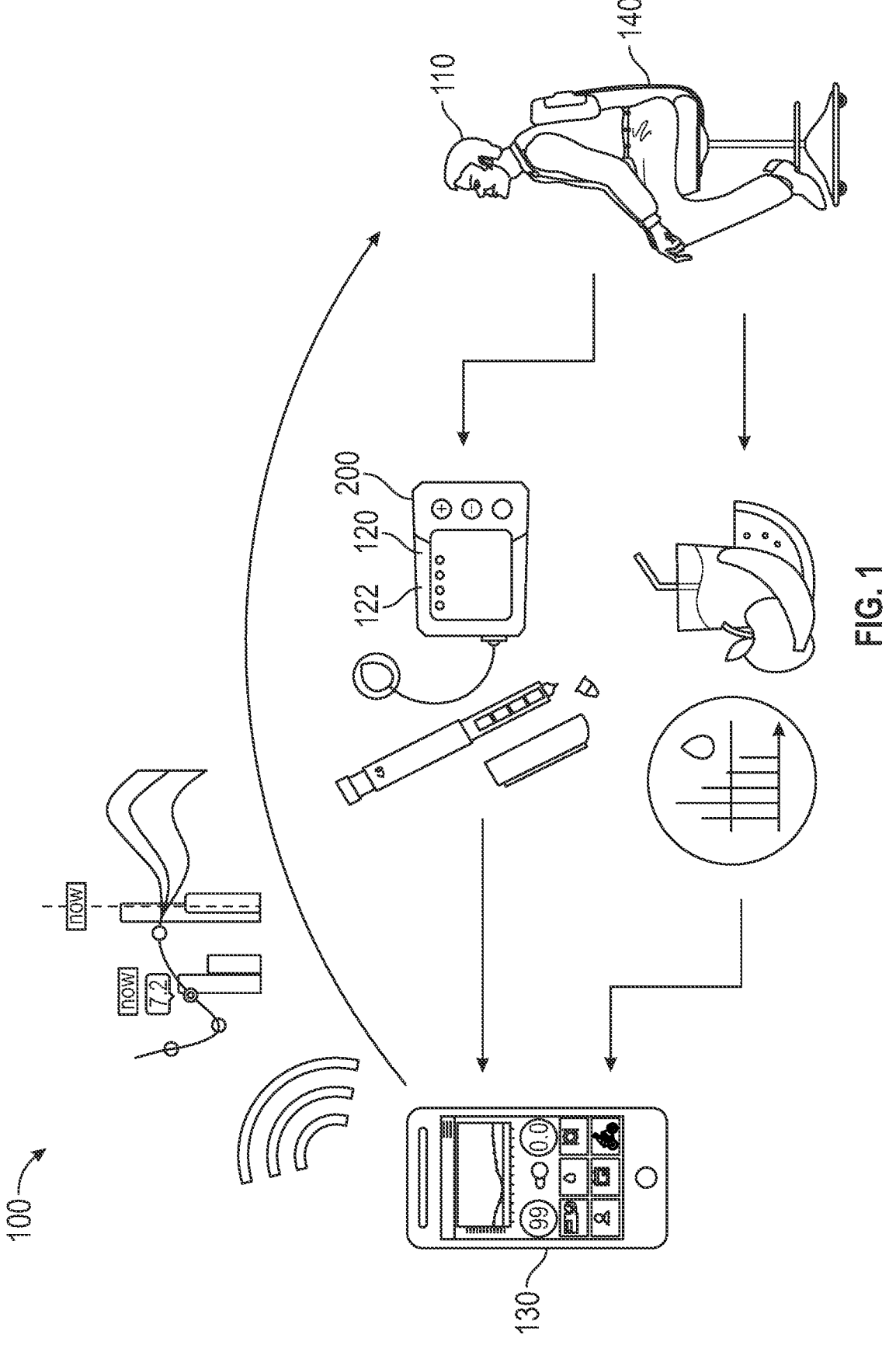
FIG. 1 is a diagram of a system for predicting blood-glucose concentration according to aspects of the disclosure.

The present disclosure relates to systems and methods for data augmentation, specifically for data augmentation using mean-field games.

Aspects of the present disclosure are described in detail with reference to the drawings wherein like reference numerals identify similar or identical elements.

Although the present disclosure will be described in terms of specific aspects and examples, it will be readily apparent to those skilled in this art that various modifications, rearrangements, and substitutions may be made without departing from the spirit of the present disclosure. The scope of the present disclosure is defined by the claims appended hereto.

For purposes of promoting an understanding of the principles of the present disclosure, reference will now be made to exemplary aspects illustrated in the drawings, and specific language will be used to describe the same. It will nevertheless be understood that no limitation of the scope of the present disclosure is thereby intended. Any alterations and further modifications of the novel features illustrated herein, and any additional applications of the principles of the present disclosure as illustrated herein, which would occur to one skilled in the relevant art and having possession of this disclosure, are to be considered within the scope of the present disclosure.

The present disclosure relates to devices, systems, and methods for predicting the glycemic profile of a patient with type 1 diabetes (T1D) on the basis of past physiological measurements collected with minimally invasive and non-invasive on-body sensors and past therapeutic actions. Predictions are long-term and for multiple steps ahead, for example, about 30 minutes, about 60 minutes, and about 90 minutes ahead. A Convolutional Neural Network (CNN) followed by a Long Short Term Memory (LSTM) network is employed for making predications. Multiple layers of convolutional blocks are used for feature extraction, while the LSTM blocks are used for learning the temporal dynamics.

Referring to FIG. 1 a system for predicting blood-glucose concentration includes a blood-glucose monitoring device 120 including at least one sensor 122. The sensor 122 is configured to detecting current blood-glucose concentrations in the person 110. The sensor 122 may be installed about a person's body. For example, the sensor 122 may be integrally installed in an insulin pump 140 positioned about the person's body. The sensor 122 may alternatively be a disposable (e.g., a single-use sensor).

Figure 2:
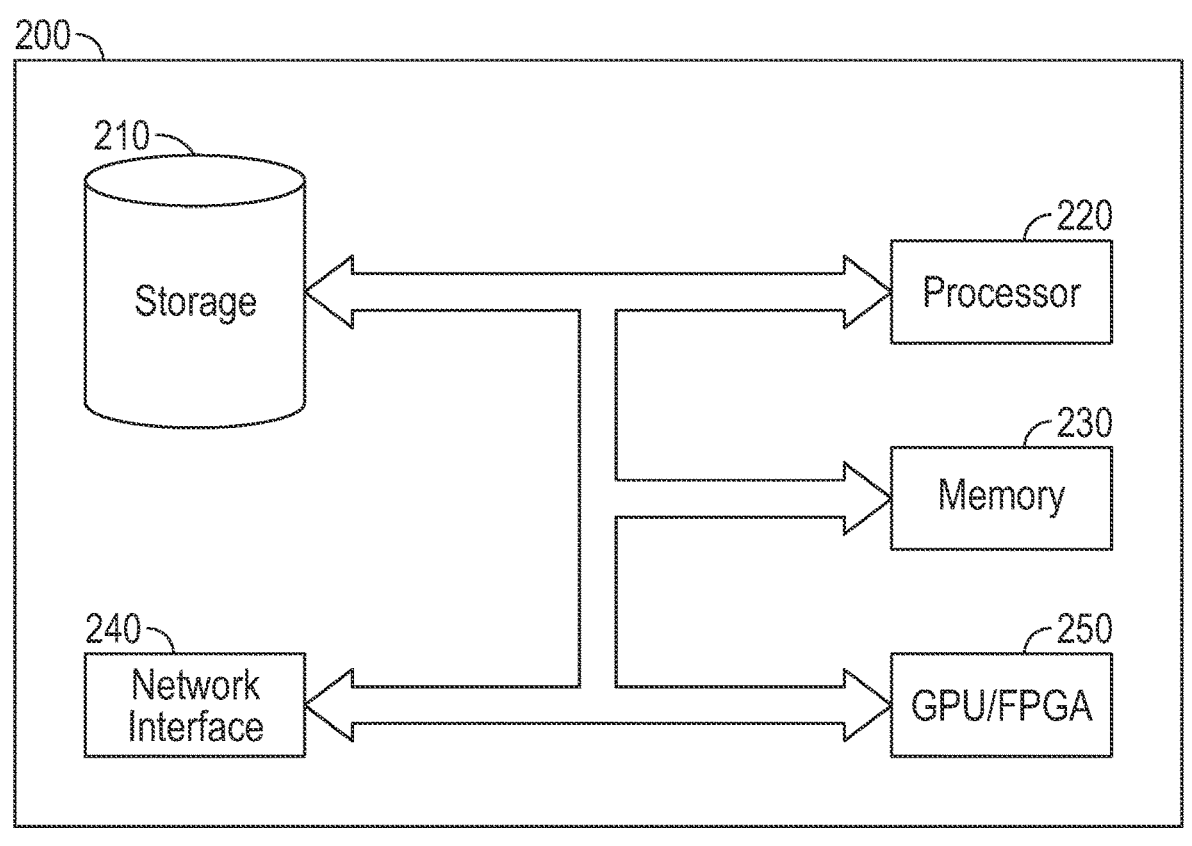
FIG. 2 is a block diagram of a controller configured for use with the system for data augmentation of FIG. 1, in accordance with aspects of the disclosure.

The blood-glucose monitoring device 120 includes a controller 200 (FIG. 2). The controller 200 may be housed in the blood-glucose monitoring device 120. An exemplary controller 200 is described in more detail below with reference to FIG. 2. The system 100 may include a user device 130 such as a smartphone, tablet computer, and/or cloud-based application in communication with the blood-glucose monitoring device. The application is configured for carrying out the method(s) described in more detail below.

FIG. 2 illustrates controller 200 includes a processor 220 connected to a computer-readable storage medium or a memory 230. The controller 200 may be used to control and/or execute operations of the system 100. The computer-readable storage medium or memory 230 may be a volatile type of memory, e.g., RAM, or a non-volatile type of memory, e.g., flash media, disk media, etc. In various aspects of the disclosure, the processor 220 may be another type of processor, such as a digital signal processor, a microprocessor, an ASIC, a graphics processing unit (GPU), a field-programmable gate array (FPGA), or a central processing unit (CPU). In certain aspects of the disclosure, network inference may also be accomplished in systems that have weights implemented as memristors, chemically, or other inference calculations, as opposed to processors.

In aspects of the disclosure, the memory 230 can be random access memory, read-only memory, magnetic disk memory, solid-state memory, optical disc memory, and/or another type of memory. In some aspects of the disclosure, the memory 230 can be separate from the controller 200 and can communicate with the processor 220 through communication buses of a circuit board and/or through communication cables such as serial ATA cables or other types of cables. The memory 230 includes computer-readable instructions that are executable by the processor 220 to operate the controller 200. In other aspects of the disclosure, the controller 200 may include a network interface 240 to communicate with other computers or to a server. A storage device 210 may be used for storing data. The disclosed method may run on the controller 200 or on a user device, including, for example, on a mobile device, an IoT device, or a server system.

Figure 3:
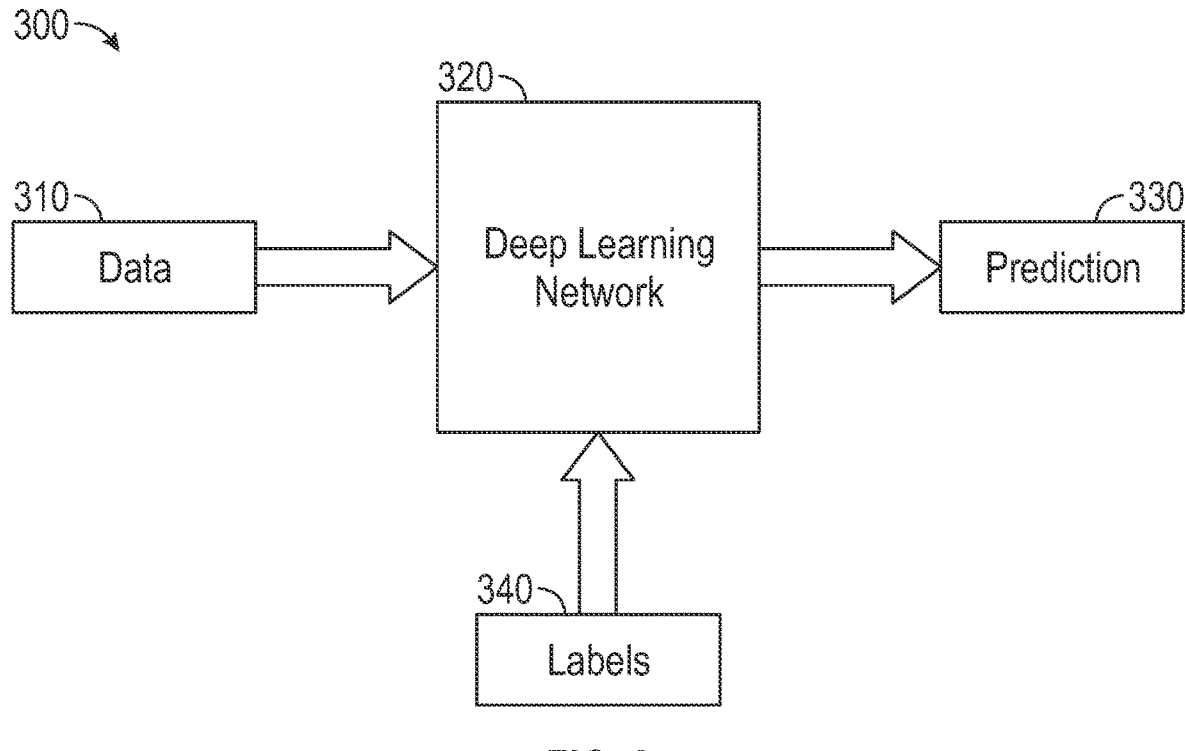
FIG. 3 is a block diagram of a deep learning network with inputs and outputs of a deep learning neural network, in accordance with aspects of the present disclosure.

With reference to FIG. 3, a block diagram for a deep learning network 320 for classifying data in accordance with some aspects of the disclosure is shown. In some systems, a deep learning network 320 may include, for example, a convolutional neural network (CNN) and/or a recurrent neural network. A deep learning neural network includes multiple hidden layers. As explained in more detail below, the deep learning network 320 may leverage one or more classification models (e.g., CNNs, decision trees, Naive Bayes, k-nearest neighbor) to classify data. The deep learning network 320 may be executed on the controller 200 (FIG. 2). Persons skilled in the art will understand the deep learning network 320 and how to implement it.

In machine learning, a CNN is a class of artificial neural network (ANN), most commonly applied to analyzing visual imagery. The convolutional aspect of a CNN relates to applying matrix processing operations to localized portions of an image, and the results of those operations (which can involve dozens of different parallel and serial calculations) are sets of many features that are delivered to the next layer. A CNN typically includes convolution layers, activation function layers, deconvolution layers (e.g., in segmentation networks), and/or pooling (typically max pooling) layers to reduce dimensionality without losing too many features. Additional information may be included in the operations that generate these features. Providing unique information that yields features that give the neural networks information can be used to provide an aggregate way to differentiate between different data input to the neural networks. The deep learning network may include a convolutional long short-term memory neural network (CNN-LSTM). Although CNNs are used as an example, other machine learning classifiers are contemplated.

The deep learning network 320 may be trained based on labeling training data to optimize weights. For example, samples of blood-glucose sensor feature data may be taken and labeled using other blood-glucose sensor feature data. In some methods in accordance with this disclosure, the training may include supervised learning or semi-supervised. Persons skilled in the art will understand training the deep learning network 320 and how to implement it.

Referring to FIG. 4, a flow diagram for a method in accordance with the present disclosure for predicting blood-glucose concentration 500 is shown. Although the steps of FIG. 4 are shown in a particular order, the steps need not all be performed in the specified order, and certain steps can be performed in another order. For example, FIG. 4 will be described below, with a controller 200 of FIG. 2 performing the operations. In aspects, the operations of FIG. 4 may be performed all or in part by another device, for example, a server, and/or a computer system. These variations are contemplated to be within the scope of the present disclosure.

Initially, at step 502 the controller accesses data of meal intake for a person with type 1 diabetes. For example, the meal intake data may be entered by the patient and or a clinician. The meal intake data may be stored locally on the memory of the blood-glucose monitoring device 120 (FIG. 1).

Next, at step 504, the controller 200 accesses data of insulin doses administered to the person 110. Next, at step 506, the controller 200 accesses data of blood-glucose levels in the person 110. The data of blood-glucose levels may be measured using sensor 122 of the blood-glucose monitoring device 120 (FIG. 1). The controller 200 may access data corresponding to physical activity data of the person 110, such as accelerometer data, gyroscope data, and/or data indicating a stress state.

Next, at step 506, the controller 200 determines by a deep learning network blood-glucose concentration levels for the person 110 at a plurality of predetermined time intervals based on the accessed data of meal intake, the accessed data of insulin doses, and the accessed data of blood-glucose levels in the person. In aspects, a deep learning network may include a convolutional long short-term memory neural network (CNN-LSTM). The CNN-LSTM may perform an analysis on the provided data of meal intake, the provided data of insulin doses and the provided data of blood-glucose levels in the person, to provide a prediction of blood-glucose concentration levels. The blood-glucose concentration levels may be predicted for the person at a plurality of predetermined time intervals based on the CNN-LSTM analysis.

Next at step 510, the controller 200 determines an insulin administration schedule based on the predicted blood-glucose concentration levels for the person 110. The insulin administration schedule may include a dosing schedule.

Next at step 512, the controller 200 administers insulin to the person 110 according to the determined insulin administration schedule. For example, the insulin may be administered to the person 110 by an insulin pump 140. The insulin pump may administer insulin according to the dosing schedule in an automated manner and without intervention by the person 110. Alternatively, the insulin schedule may be administered by manually injecting insulin into the person.

In an aspect of the present disclosure, the insulin administration schedule may be communicated to the person prior to starting the dosing schedule. For example, a smartphone or table computer application may communicate the proposed insulin administration schedule to the person on a display for approval by the person or so that the person can manually administer insulin according to the schedule. The data of insulin doses administered to the person may include data of bolus doses and correction doses received by the person during a predetermined time period.

Real-time blood glucose concentrations can be detected in the person during the insulin administration schedule (e.g., by employing the sensors described herein) and then the insulin administration schedule can be modified based on the detected real-time blood glucose concentrations in the person.

In an aspect of the present disclosure, the data of meal intake includes data of lipid, carbohydrate, and protein intake. For example, quantitative values and proportions of ingested lipids, carbohydrates and proteins can be employed by the CNN-LSTM model described herein for predicting blood glucose concentrations.

As an example, the predetermined time intervals at which blood glucose concentration is predicted includes about 30-minute, about 60-minute and about 90-minute time intervals.

In aspects, the controller 200 may provide historical glucose metabolism data for the person and including the historical glucose metabolism data in the CNN-LSTM analysis.

Figure 5:
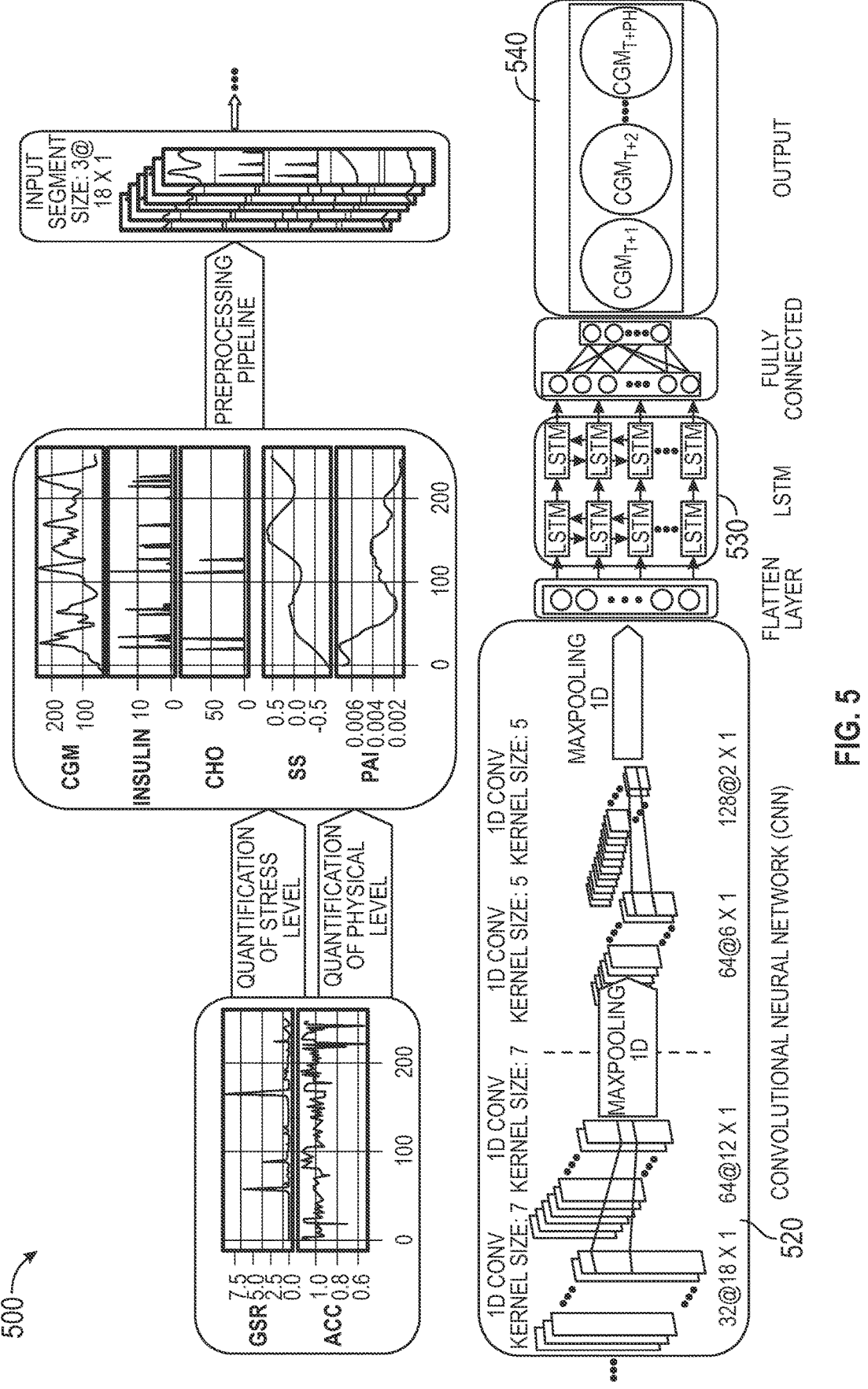
FIG. 5 is a diagram of a Convolutional Neural Network (CNN) followed by a Long Short Term Memory (LSTM) network is employed for making predications, in accordance with aspects of the disclosure.

Referring to FIG. 5, a diagram of an exemplary deep learning network 600 employed for making predications is shown. The deep learning network 600 may include a CNN 620 followed by an LSTM network 630. For example, the method 500 of predicting blood-glucose concentrations described herein may employ a stacked CNN-LSTM hybrid architecture including multiple layers of convolutional blocks used for feature extraction and LSTM blocks for learning temporal dynamics.

A CNN 620 generally includes convolutional layers in which a kernel of numbers is rolled over the input matrices and outputs a feature map, pooling layers which decrease the size of the feature maps to reduce the computational cost and fully connected layers that are in fact embedding layers which encode all of the features that are extracted by the convolutional and pooling layers. Using this concept and by employing a sliding window, window shaped samples may be extracted from the time series dataset at hand, and make the data ready to be fed to a CNN model.

The LSTM network 630 is a developed type of a recurrent neural network (RNN) with memory blocks which let the network remember previous states in a dataset. Activation functions in an LSTM unit are functions of previous states of the model, such that they make a short-term memory. Each LSTM block has three gates, input, output and forget gates, which are also connected with previous and next cells and are responsible for controlling the information flow in the block. LSTM models are generally applied in natural language processing (NLP) problems, where the semantic connection between the words should be learned. However, being powerful in learning the temporal patterns, LSTM may also be applied in multivariate time series where the causal effect of variables on each other are necessary to be discovered.

The combined CNN-LSTM model (deep learning network) 600 may include a stack of one dimensional convolutional and pooling layers, followed by LSTM units and fully connected layers. Using two groups of two back-to-back convolutional layers may increase the chance of extracting underlying features of the input samples based on their significance. Extracted features may then be flattened to one long vector and fed to a group of two LSTM layers which due to having short-term memory, can analyze and forecast sequences via a recurrent procedure. The output of the LSTM section is passed through a group of two fully connected layers, which act like a buffer between the learned features and the desired output, and interpret them such that a prediction of the future glucose value is achieved.

Referring to FIG. 6, is a diagram of an exemplary deep learning network 700. In aspects, the deep learning network may include two serial LSTM networks 730 employed for making predictions, with raw acceleration (ACC), e.g., an accelerometer, and an electrodermal activity (EDA) signals used to estimate physical activity intensity (PAI) and stress state (SS) features, respectively. The generated features, along with the continuous glucose monitoring (CGM), insulin, and carbohydrate (CHO) signals, are passed through the preprocessing pipeline for interpolation, standardization, and generating windowed-sampled input segments. Batches of input segments are fed to the proposed DL model. After passing through the CNN section, significant features extracted from the data are flattened into an array and passed towards a stack of two LSTM layers (e.g., serial LSTM networks 730) where temporal dynamics and dependency between the variables are learned by the model. Finally, via two fully connected layers, features are embedded and encoded such that at the future glucose concentration values are predicted.

Referring to FIG. 7, a table of population results for the LSTM model of FIG. 6 is shown. Obtained accuracy metrics for forecasting the GC level for about 30, about 60, and about 90 minutes PH, for different scenarios include: average mean absolute error (MAE) [mg/dL], root mean square error (RMSE) [mg/dL], and coefficient of determination (R2) [%]. FIG. 8 is a table of population results for the CNN-LSTM model of FIG. 5.

Referring to FIG. 9, a table of a patient-wise results with the LSTM model of FIG. 6, is shown. MAE, RMSE and R2 of GC prediction for personalized training for each patient separately, for about 30, about 60, and about 90 minutes PH. Referring to FIG. 10, a table of a patient-wise results with the CNN-LSTM model of FIG. 5 is shown.

Certain aspects of the present disclosure may include some, all, or none of the above advantages and/or one or more other advantages readily apparent to those skilled in the art from the drawings, descriptions, and claims included herein. Moreover, while specific advantages have been enumerated above, the various aspects of the present disclosure may include all, some, or none of the enumerated advantages and/or other advantages not specifically enumerated above.

The aspects disclosed herein are examples of the disclosure and may be embodied in various forms. For instance, although certain aspects herein are described as separate aspects, each of the aspects herein may be combined with one or more of the other aspects herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an aspect," "in aspects," "in various aspects," "in some aspects," or "in other aspects" may each refer to one or more of the same or different example Aspects provided in the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The aspects described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A system for predicting blood-glucose concentration, comprising:
    a blood-glucose monitoring device including at least one sensor configure to capture blood-glucose levels, a processor, and a memory storing instructions, which, when executed by the processor, cause the system to:

access data of meal intake for a person with type 1 diabetes;

access data of insulin doses administered to the person;

access data corresponding to a physical activity of the person;

access data of blood-glucose levels in the person, captured by the sensor;

predict by a deep learning network blood-glucose concentration levels for the person at a plurality of predetermined time intervals based on the accessed data of meal intake, the accessed data of insulin doses, the accessed data corresponding to the physical activity, and the accessed data of blood-glucose levels in the person, wherein the deep learning network includes a convolutional neural network feeding a long short-term memory network; and determine an insulin administration schedule based on the predicted blood-glucose concentration levels for the person, the insulin administration schedule including a dosing schedule.

2. The system of claim 1, further including an insulin pump, wherein the instructions, when executed by the processor, further cause the system to:

cause the insulin pump to administer insulin according to the insulin administration schedule to the person.

3. The system of claim 1, wherein the instructions, when executed by the processor, further cause the system to communicate the insulin administration schedule to the person.

4. The system of claim 1, wherein the instructions, when executed by the processor, further cause the system to:

detect real-time blood glucose concentrations in the person during the insulin administration schedule and modifying the insulin administration schedule based on the detected real-time blood glucose concentrations in the person.

5. The system of claim 1, wherein the data of meal intake accessed by the processor includes data of lipid, carbohydrate, and protein intake.

6. The system of claim 1, wherein the instructions, when executed by the processor, further cause the system to:

predict blood-glucose concentration levels for the person at about 30-minute, about 60-minute, and about 90-minute time intervals.

7. The system of claim 1, wherein the instructions, when executed by the processor, further cause the system to:

receive historical glucose metabolism data for the person and include the historical glucose metabolism data as a further input to the deep learning network.

8. The system of claim 1, wherein the instructions, when executed by the processor, further cause the system to:

receive data of bolus doses and correction doses received by the person during a predetermined time period.

9. The system of claim 1, further including at least one of a smartphone, tablet computer, or cloud-based application in communication with the blood-glucose monitoring device.

10. The system of claim 1, wherein the deep learning network includes at least two long short-term memory networks.

11. A computer-implemented method for predicting blood-glucose concentration, comprising:

accessing data of meal intake for a person with type 1 diabetes;

accessing data of insulin doses administered to the person;

accessing data corresponding to a physical activity of the person;

accessing data of blood-glucose levels in the person;

predicting by a deep learning network blood-glucose concentration levels for the person at a plurality of predetermined time intervals based on the accessed data of meal intake, the accessed data of insulin doses, the accessed data corresponding to the physical activity, and the accessed data of blood-glucose levels in the person, wherein the deep learning network includes a convolutional neural network feeding a long short-term memory network; and determining an insulin administration schedule based on the predicted blood-glucose concentration levels for the person, the insulin administration schedule including a dosing schedule.

12. The computer-implemented method of claim 11, further including administering insulin to the person according to the determined insulin administration schedule.

13. The computer-implemented method of claim 12, wherein the insulin administered to the person is administered by an insulin pump.

14. The computer-implemented method of claim 12, further including communicating the insulin administration schedule to the person.

15. The computer-implemented method of claim 12, further including detecting real-time blood glucose concentrations in the person during the insulin administration schedule and modifying the insulin administration schedule based on the detected real-time blood glucose concentrations in the person.

16. The computer-implemented method of claim 11, wherein the data of meal intake includes data of lipid, carbohydrate, and protein intake.

17. The computer-implemented method of claim 11, wherein the plurality of predetermined time intervals includes about 30-minute, about 60-minute, and about 90-minute time intervals.

18. The computer-implemented method of claim 11, further including providing historical glucose metabolism data for the person and including the historical glucose metabolism data as a further input to the deep learning network.

19. The computer-implemented method of claim 11, wherein the data of insulin doses administered to the person include data of bolus doses and correction doses received by the person during a predetermined time period.

20. A non-transitory computer-readable medium storing instructions which, when executed by a processor, cause the processor to perform a computer-implemented method for predicting blood-glucose concentration, comprising:

accessing data of meal intake for a person with type 1 diabetes;

accessing data of insulin doses administered to the person;

accessing data corresponding to a physical activity of the person;

accessing data of blood-glucose levels in the person;

predicting by a deep learning network blood-glucose concentration levels for the person at a plurality of predetermined time intervals based on the accessed data of meal intake, the accessed data of insulin doses, the accessed data corresponding to the physical activity, and the accessed data of blood-glucose levels in the person, wherein the deep learning network includes a convolutional neural network feeding a long short-term memory network; and determining an insulin administration schedule based on the predicted blood-glucose concentration levels for the person, the insulin administration schedule including a dosing schedule.

* * * * *